United States Patent
Srinivas et al.

(10) Patent No.: US 8,223,916 B2
(45) Date of Patent: Jul. 17, 2012

(54) COMPUTER-AIDED DETECTION OF ANATOMICAL ABNORMALITIES IN X-RAY TOMOSYNTHESIS IMAGES

(75) Inventors: Chukka Srinivas, San Jose, CA (US); Julian Marshall, Los Altos, CA (US); Xiangwei Zhang, Sunnyvale, CA (US); Haili Chui, Sunnyvale, CA (US); Kevin A. Kreeger, Sunnyvale, CA (US); Wei Zhang, Union City, CA (US)

(73) Assignee: Hologic, Inc., Marlborough, MA (US)

( * ) Notice: Subject to any disclaimer, the term of this patent is extended or adjusted under 35 U.S.C. 154(b) by 591 days.

(21) Appl. No.: 12/415,972

(22) Filed: Mar. 31, 2009

(65) Prior Publication Data

US 2010/0246913 A1    Sep. 30, 2010

(51) Int. Cl.
*A61B 6/04* (2006.01)

(52) U.S. Cl. ............................................ 378/37; 378/21
(58) Field of Classification Search .................. 382/131, 382/132; 378/4, 21, 37
See application file for complete search history.

(56) References Cited

U.S. PATENT DOCUMENTS

| | | | |
|---|---|---|---|
| 5,729,620 A | 3/1998 | Wang | |
| 5,815,591 A | 9/1998 | Roehrig et al. | |
| 5,917,929 A | 6/1999 | Marshall et al. | |
| 6,014,452 A | 1/2000 | Zhang et al. | |
| 6,075,879 A | 6/2000 | Roehrig et al. | |
| 6,301,378 B1 | 10/2001 | Karssemeijer et al. | |
| 6,574,357 B2 | 6/2003 | Wang | |
| 6,748,044 B2 * | 6/2004 | Sabol et al. | 378/4 |
| 7,142,633 B2 | 11/2006 | Eberhard et al. | |
| 7,218,766 B2 | 5/2007 | Eberhard et al. | |
| 2003/0194121 A1 | 10/2003 | Eberhard et al. | |
| 2003/0215120 A1 | 11/2003 | Uppaluri et al. | |
| 2005/0002550 A1 | 1/2005 | Jabri et al. | |
| 2005/0089205 A1 | 4/2005 | Kapur et al. | |
| 2005/0113961 A1 | 5/2005 | Sabol et al. | |
| 2005/0135664 A1 * | 6/2005 | Kaufhold et al. | 382/131 |
| 2006/0067473 A1 | 3/2006 | Eberhard et al. | |
| 2006/0210131 A1 | 9/2006 | Wheeler et al. | |
| 2006/0269114 A1 | 11/2006 | Metz | |
| 2006/0291711 A1 | 12/2006 | Jabri et al. | |

(Continued)

OTHER PUBLICATIONS

McCloughlin, K., et. al., "Noise Equalization for Detection of Microcalcification Clusters in Direct Digital Mammogram Images," IEEE Trans. Med. Imag., vol. 23, No. 3, pp. 313-320 (2004).

*Primary Examiner* — Tarifur Chowdhury
*Assistant Examiner* — Jonathan Hansen
(74) *Attorney, Agent, or Firm* — Vista IP Law Group LLP

(57) ABSTRACT

Methods, systems, and related computer program products for computer-aided detection (CAD) of anatomical abnormalities in a breast volume based on a plurality of two-dimensional x-ray tomosynthesis projection images thereof is described. Each projection image is processed according to at least one predetermined feature extraction algorithm to generate at least one projection feature array corresponding thereto. For each of the at least one predetermined features extracted, the plurality of corresponding projection feature arrays is backprojected according to a predetermined tomosynthesis reconstruction algorithm to form a plurality of two-dimensional tomosynthesis reconstructed feature arrays. Each pixel in the three-dimensional breast geometry is then individually classified as being either a pixel of interest, or not a pixel of interest, based upon the at least one tomosynthesis reconstructed feature array value corresponding to that pixel. CAD detections for the breast volume are then generated based on the identified pixels of interest.

20 Claims, 5 Drawing Sheets

U.S. PATENT DOCUMENTS

| | | |
|---|---|---|
| 2007/0003117 A1 | 1/2007 | Wheeler et al. |
| 2007/0003118 A1 | 1/2007 | Wheeler et al. |
| 2007/0014448 A1 | 1/2007 | Wheeler et al. |
| 2007/0052700 A1 | 3/2007 | Wheeler et al. |
| 2007/0076928 A1 | 4/2007 | Claus et al. |
| 2008/0025592 A1 | 1/2008 | Jerebko et al. |
| 2010/0067754 A1* | 3/2010 | Collins et al. .................. 382/128 |
| 2010/0166267 A1* | 7/2010 | Zhang et al. .................. 382/128 |

* cited by examiner

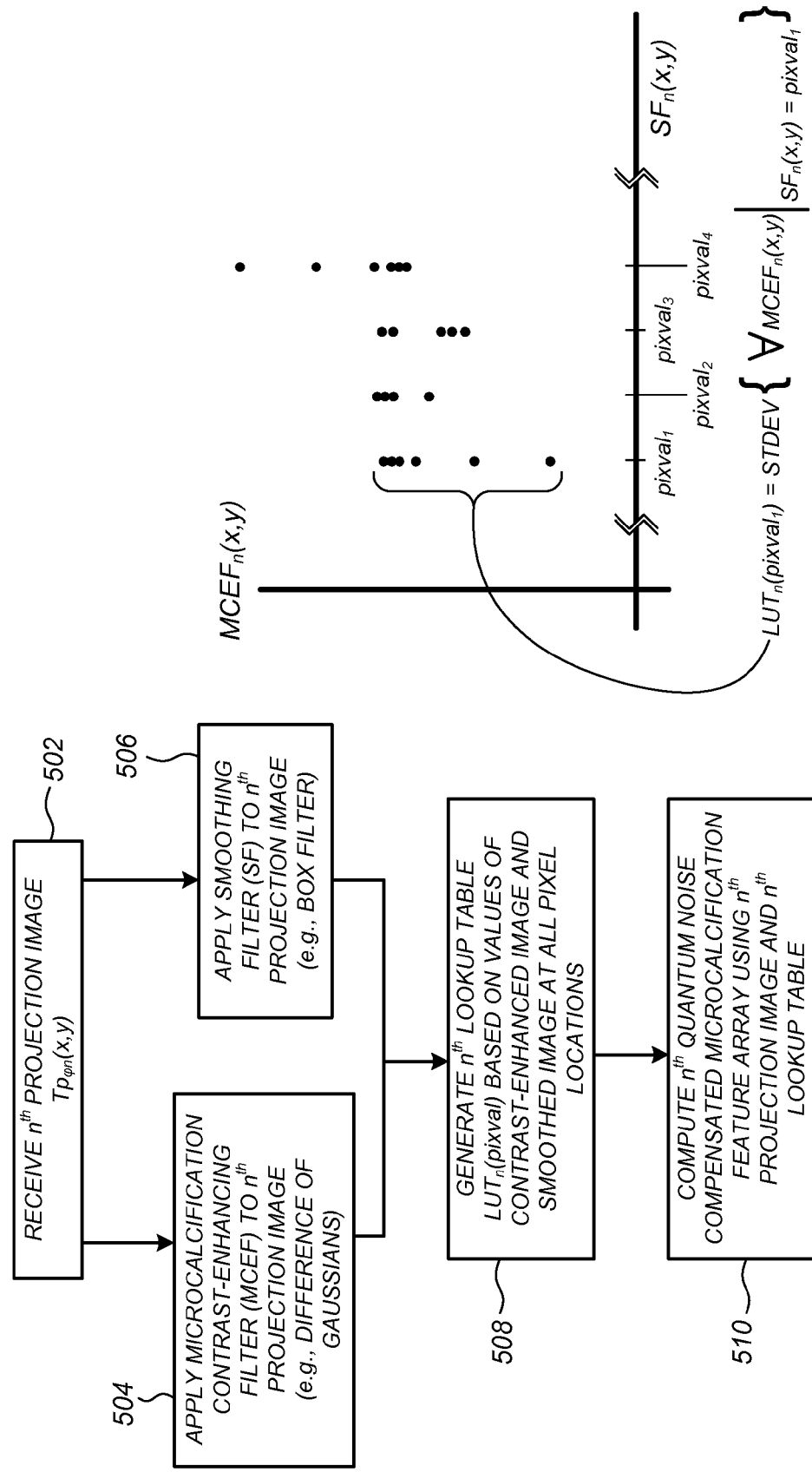

COMPUTER-AIDED DETECTION OF ANATOMICAL ABNORMALITIES IN X-RAY TOMOSYNTHESIS IMAGES

FIELD

This patent specification relates to the processing of medical images. More particularly, this patent specification relates to the computer-aided detection of anatomical abnormalities in x-ray tomosynthesis images.

BACKGROUND

Breast cancer is a serious health problem, the American Cancer Society currently estimating that over 182,000 U.S. women are diagnosed with breast cancer each year. Early detection of breast cancer is of utmost importance. Although conventional x-ray mammography is still one of the best methods for detecting early forms of breast cancer, and is the modality approved by the U.S. Food and Drug Administration (FDA) to screen for breast cancer in women who do not show symptoms of breast disease, it is still possible for cancers to be missed by the radiologist reviewing the conventional x-ray mammograms. For example, for breasts that are high in dense fibroglandular content as compared to fat content, which is common for younger and/or smaller-breasted patients, conventional x-ray mammograms often contain saturated bright areas that can obscure cancerous conditions.

For these and other reasons, substantial attention and technological effort has been dedicated toward breast x-ray tomosynthesis, which is similar in many respects to conventional x-ray mammography except that, for any particular view such as the CC or MLO view, the x-ray source is no longer stationary, but instead rotates through a limited angle relative to the breast platform normal (e.g., −15 degrees to +15 degrees) while several projection images (e.g., 10-15 projection images) are acquired by the x-ray detector. The several projection images are then mathematically processed to yield a relatively high number (e.g., 40-60) of tomosynthesis reconstructed images, each corresponding to a different slice of breast tissue, which can then be examined by the radiologist. Whereas a particular cancerous lesion positioned within a region of dense fibroglandular tissue might have been obscured in a single conventional x-ray mammogram view, that lesion could be readily apparent within a set of tomosynthesis reconstructed images representative of individual slices through the dense fibroglandular tissue. Examples of breast x-ray tomosynthesis systems can be found in U.S. Pat. No. 5,872,828, U.S. Pat. No. 7,123,684, and U.S. Pat. No. 7,245,694, each of which is incorporated by reference herein.

Computer-aided detection (CAD) refers to the use of computers to analyze medical images to detect anatomical abnormalities therein. Sometimes used interchangeably with the term computer-aided detection are the terms computer-aided diagnosis, computer-assisted diagnosis, or computer-assisted detection. The outputs of CAD systems are sets of information sufficient to communicate the locations of anatomical abnormalities, or lesions, in a medical image, and can also include other information such as the type of lesion, degree of suspiciousness, and the like. Such CAD detections are most often communicated in the form of graphical annotations overlaid upon diagnostic-quality and/or reduced-resolution versions of the medical image. CAD results are mainly used by radiologists as "secondary reads" or secondary diagnosis tools. Some CAD implementations, however, have used CAD results in a "concurrent reading" context in which the radiologists look at the CAD results at the same time that they look at the images. Thousands of CAD systems for conventional x-ray mammography are now installed worldwide, and are used to assist radiologists in the interpretation of millions of mammograms per year. X-ray mammography CAD systems are described, for example, in U.S. Pat. No. 5,729,620, U.S. Pat. No. 5,815,591, U.S. Pat. No. 5,917,929, U.S. Pat. No. 6,014,452, U.S. Pat. No. 6,075,879, U.S. Pat. No. 6,301,378, and U.S. Pat. No. 6,574,357, each of which is incorporated by reference herein.

CAD-assisted reading of medical images can be particularly important in the context of x-ray tomosynthesis imaging, where the number of medical images to be read by the radiologist is substantially greater than for conventional x-ray mammography. Various proposals for achieving x-ray tomosynthesis CAD have been set forth, for example, in U.S. Pat. No. 6,748,044, U.S. Pat. No. 7,218,766, US 20070052700A1, and US20080025592A1, each of which is incorporated by reference herein.

However, x-ray tomosynthesis image data sets represent unique collections of information that can bring about many pitfalls in the implementation of automated abnormality detection routines thereon. For example, as compared to conventional x-ray mammography images, tomosynthesis projection images tend to suffer from high amounts of quantum noise because of the reduced x-ray dosages involved, especially in high-density tissue areas. Particularly in the context of automated microcalcification detection, the high amount of quantum noise can lead to a high false positive rate and/or substantial computational inefficiencies in eliminating false positives. As another example, consistent with the equivocal "tomosynthesis" moniker, tomosynthesis reconstructed images carry with them a substantial number of reconstruction-related artifacts that would not be present if they were truly "tomography" images, and these artifacts can also confound certain CAD algorithms that focus too heavily upon the tomosynthesis reconstructed image data.

One particular challenge in implementing x-ray tomosynthesis CAD relates to making an initial determination of which pixels in the tomosynthesis reconstructed data set are "pixels of interest" that deserve further consideration by the many complex and time-consuming downstream processes in the CAD algorithm, such as processes that group the pixels together, arrange those groups into candidate anomaly lists, and extensively process the candidate anomalies to generate the ultimate set of CAD detections. On the one hand, if the initial determination algorithm is too inclusive, the overall efficiency of the CAD algorithm can suffer as the downstream algorithms process the overly long candidate anomaly lists. On the other hand, if the initial determination algorithm is too exclusionary, then the overall sensitivity of the CAD algorithm is reduced, i.e., truly suspicious lesions might be missed because the associated pixels were discarded in the initial determination algorithm. Achieving sensitive yet specific initial identification of the "pixels of interest" is particularly challenging in view of the substantial quantum noise present in the tomosynthesis projection images, together with the substantial artifacts that may be present in the tomosynthesis reconstructed images. Other issues arise as would be apparent to a person skilled in the art in view of the present disclosure.

SUMMARY

According to one preferred embodiment, provided is a method for computer-aided detection (CAD) of anatomical abnormalities in a breast volume based on a plurality of two-dimensional x-ray tomosynthesis projection images thereof acquired at a respective plurality of x-ray tomosynthesis projection angles. Each of the plurality of projection images is processed separately from the other projection images according to at least one predetermined feature extraction algorithm to generate at least one projection feature array corresponding thereto. For each of the at least one predetermined features extracted, the plurality of corresponding projection feature arrays is backprojected according to a predetermined tomosynthesis reconstruction algorithm to form a plurality of two-dimensional tomosynthesis reconstructed feature arrays, the imaged breast volume having a three-dimensional geometry characterized by a number of levels and a number of pixels per level, wherein the plurality of two-dimensional tomosynthesis reconstructed feature arrays collectively occupy that three-dimensional geometry. Each pixel in each level of the three-dimensional geometry is then individually classified as being either a pixel of interest, or not a pixel of interest, based upon the at least one tomosynthesis reconstructed feature array value corresponding to that pixel location. CAD detections for the breast volume are then generated based on the identified pixels of interest.

Also provided is a system for detecting suspicious microcalcifications in a breast volume based on a plurality of two-dimensional x-ray tomosynthesis projection images thereof acquired at a respective plurality of x-ray tomosynthesis projection angles, the system comprising a processor programmed to jointly process the plurality of projection images to generate a noise compensation function based on joint noise statistics in the plurality of projection images, and to process each of the plurality of projection images using a microcalcification-enhancing filter, a spatial smoothing filter, and the noise compensation function to generate a respective plurality of projection noise-compensated microcalcification feature arrays. The processor then backprojects the plurality of projection noise-compensated microcalcification feature arrays according to a predetermined tomosynthesis reconstruction algorithm to form a plurality of two-dimensional tomosynthesis reconstructed feature arrays, the imaged breast volume having a three-dimensional geometry characterized by a number of levels and a number of pixels per level, wherein the plurality of two-dimensional tomosynthesis reconstructed feature arrays collectively occupy the three-dimensional geometry. The processor then individually classifies each pixel in each level of the three-dimensional geometry as being either a pixel of interest or not a pixel of interest based upon the at least one tomosynthesis reconstructed feature array value corresponding to that pixel location. The processor then further processes the identified pixels of interest to detect suspicious microcalcifications in the breast volume.

BRIEF DESCRIPTION OF THE DRAWINGS

FIG. 5 illustrates a method for computing a projection quantum noise compensated microcalcification feature array according to a preferred embodiment; and FIG. 6 illustrates a scatter plot corresponding to the method of FIG. 5.

DETAILED DESCRIPTION

Figure 1:
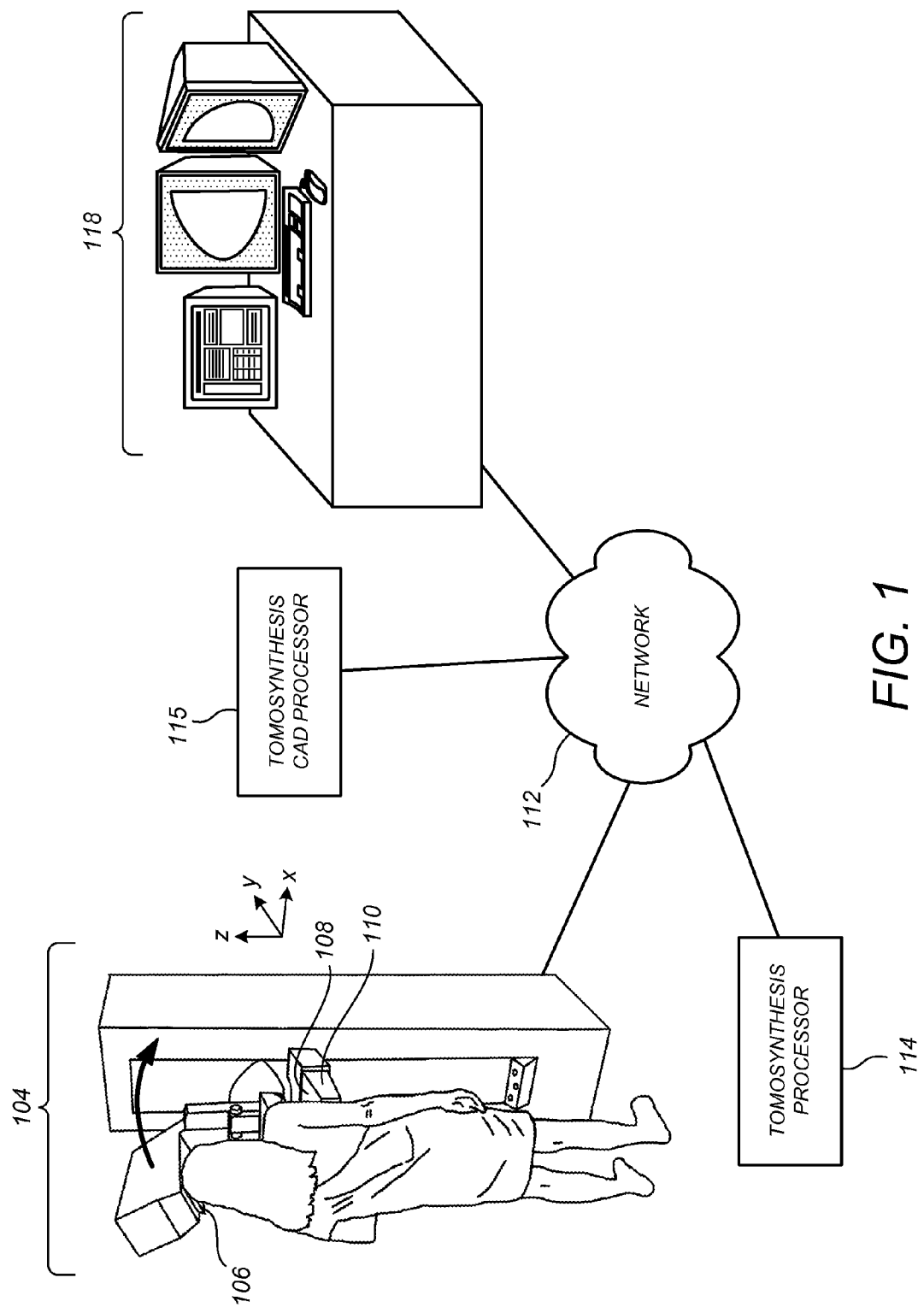
FIG. 1 illustrates a conceptual diagram of a breast x-ray tomosynthesis imaging environment including a tomosynthesis CAD processor according to a preferred embodiment.

FIG. 1 illustrates a conceptual diagram of a breast x-ray tomosynthesis imaging environment including CAD capability for which one or more of the preferred embodiments described further herein are particularly suited. Shown in FIG. 1 is a network 112, which may be a HIS/RIS (Hospital Information System/Radiology Information System) network, to which is coupled a breast x-ray tomosynthesis acquisition device 104. The acquisition device 104 includes an x-ray source 106 projecting x-rays toward a patient's breast that is supported on a breast platform 108, along with an x-ray imager 110 underlying the breast platform 108. The x-ray source 106 is moved in an arcuate path relative to the breast platform 108 and emits x-ray radiation at specified angles therealong which are captured by the x-ray imager 110 to form a set of tomosynthesis projection images. The tomosynthesis projection images are processed by a tomosynthesis processor 114 according to one or more tomosynthesis reconstruction algorithms to form tomosynthesis reconstructed images, these images being formed and filtered with a view toward optimal visual display to a radiologist ("for presentation"). In a separate process, the tomosynthesis projection images are processed by a tomosynthesis CAD processor 115 to detect anatomical abnormalities in the breast volume. The tomosynthesis image information is then viewed in conjunction with the associated CAD results at a radiology review workstation 118.

Figure 2:
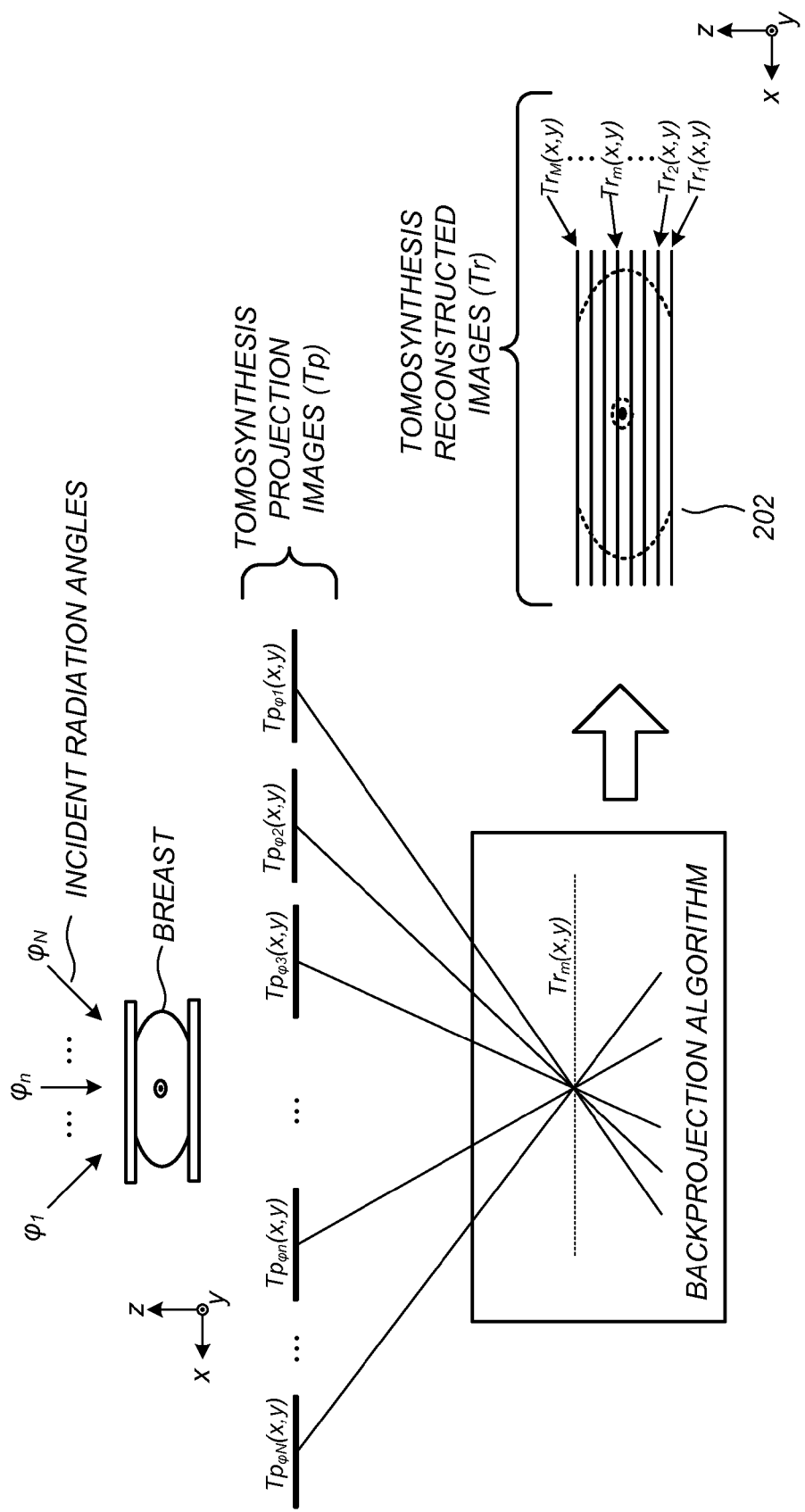
FIG. 2 illustrates examples of breast x-ray tomosynthesis projection and reconstruction geometries according to a preferred embodiment.

FIG. 2 illustrates a conceptual diagram of breast x-ray tomosynthesis projection imaging at different angles. Incident radiation impinges upon a compressed breast volume at a plurality "N" of breast x-ray tomosynthesis projection angles $\phi_n$, n=1...N, to result in a corresponding plurality "N" of tomosynthesis projection images $Tp_{\phi n}(x,y)$, n=1...N. In typical scenarios there can be N=11 or N=15 projection images, each projection image $Tp_{\phi n}(x,y)$ containing roughly 1710×2140 pixels, which would correspond to an x-ray detector that is roughly 24 cm×30 cm in size having a pixel resolution of 140 μm. It is to be appreciated that these "typical" dimensions are presented by way of example only and are not to be construed as limiting the scope of the present teachings.

Also illustrated in FIG. 2 is a three-dimensional geometry 202 for the imaged breast volume along with a conceptual icon of a tomosynthesis reconstruction algorithm in which, for a particular plane "m" having a predetermined height $h_m$ above the detection plane, the "N" projection images $Tp_{\phi n}(x,y)$, n=1...N, are processed into a two-dimensional tomosynthesis reconstructed image $Tr_m(x,y)$. More specifically, the N projection images $Tp_{\phi n}(x,y)$, n=1...N are combined by backprojection (or other tomosynthesis reconstruction algorithm) to form the tomosynthesis reconstructed image $Tr_m(x,y)$ based on that specific value of $h_m$ in a manner that highlights (e.g., does not blur) the effects of x-ray attenuating tissues located near that predetermined height $h_m$ and that de-emphasizes (e.g., blurs) x-ray attenuating tissues located away from that predetermined height $h_m$.

In theory, the number of different predetermined heights $h_m$ for which distinct two-dimensional tomosynthesis reconstructed images $Tr_m(x,y)$ can be generated is arbitrarily large, because $h_m$ is simply a selectable parameter fed to the reconstruction (backprojection) algorithm. In practice, because the ultimate amount of useful information is limited by the finite count of "N" projection images, the tomosynthesis reconstruction geometry is usually limited to a predetermined number "M" of reconstructed image arrays $Tr_m(x,y)$. Preferably, the number "M" is selected such that the reconstructed image arrays $Tr_m(x,y)$ uniformly fill out the vertical extent of the imaged breast volume between the lower and upper compression plates, at a vertical spacing (such as 1 mm) that is small enough to capture smaller-sized microcalcifications.

The lateral extent of each tomosynthesis reconstruction image $Tr_m(x,y)$, can be similar to that of each projection image $Tp_{\phi n}(x,y)$, i.e., the number of pixels and the spatial resolution of the tomosynthesis reconstructed images $Tr_m(x,y)$ can be similar as for the projection images $Tp_{\phi n}(x,y)$. However, such correspondence is not required, with super-sampling, subsampling, or other resampling being available for various reasons. For example, the particular geometries of different tomosynthesis reconstruction algorithms could be different from each other, in which case such resampling is incorporated therein as needed to cause the resultant arrays that will be being compared, added, multiplied, mapped, or otherwise jointly processed to be in registration with each other. Depending on the particular tomosynthesis reconstruction algorithm being used, the lateral resolution of the different tomosynthesis reconstructed images $Tr_m(x,y)$ can be different for different levels, for example, the uppermost level could be 95 μm per pixel while the lowermost level be 108 μm per pixel. As used herein, three-dimensional geometry of the imaged breast volume refers to a space-limited three-dimensional grid having a defined number of levels that extends at least throughout a clinically relevant portion of the breast (for example, including the breast parenchyma but excluding the skin and the empty space around the breast between the compression plates). In the event only a single predefined tomosynthesis reconstruction algorithm is involved, the three-dimensional geometry of the imaged breast volume can be based upon the number of levels in that predefined tomosynthesis reconstruction algorithm. In the event multiple predefined tomosynthesis reconstruction algorithms are involved having different geometries, the three-dimensional geometry of the imaged breast volume can be based on one of them, with resampling being incorporated into the others to result in appropriate registration. Alternatively, the three-dimensional geometry of the imaged breast volume could be based on the tomosynthesis reconstruction algorithms that were, or will be, used to generate the "for presentation" tomosynthesis reconstructed images.

Figure 3:
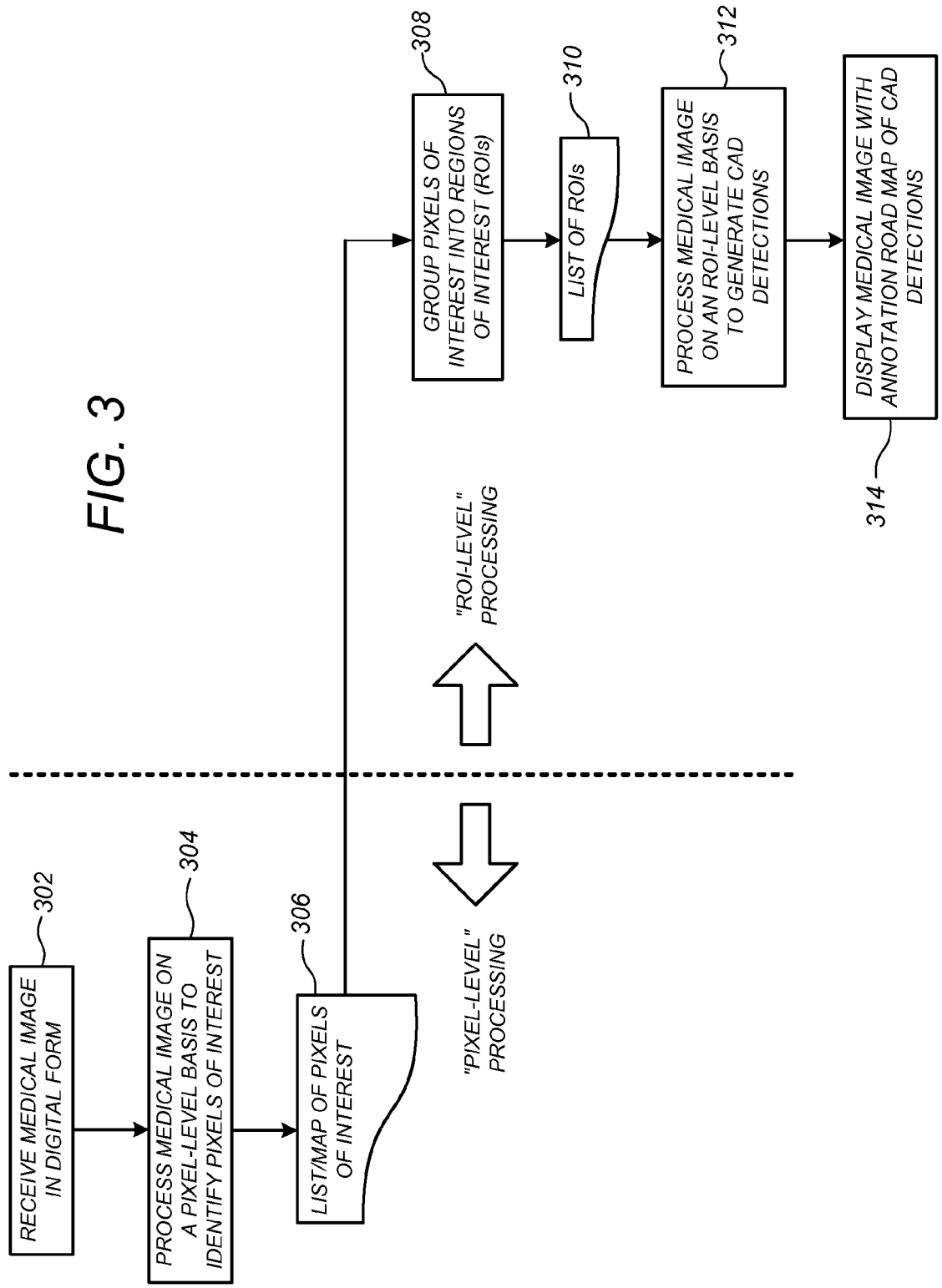
FIG. 3 illustrates an x-ray tomosynthesis CAD algorithm including pixel-level analysis steps and ROI-level analysis.

FIG. 3 illustrates an overall architecture of an x-ray tomosynthesis CAD algorithm as programmed for detecting any particular type of anatomical abnormality, such as suspicious microcalcifications or suspicious masses. The CAD algorithm generally comprises two overall phases, which are termed herein pixel-level processing and ROI-level processing. In the pixel-level processing phase at the left side of FIG. 3, x-ray tomosynthesis projection images received at step 302 are processed at step 304 to identify pixels of interest in the three-dimensional breast geometry, resulting in a list or map of "pixels of interest" at step 306. The list or map of pixels of interest (which can alternatively be called pixels of concern, suspicious pixels, or starting pixels) is then provided to an ROI-level processing phase at the right side of FIG. 3. Pixels of interest are grouped into regions of interest (ROIs) at step 308 to result in a list of ROIs at step 310, and these ROIs along with the tomosynthesis projection images and various desired reconstructions thereof are further processed at step 312 to generate CAD detections, which are then available for output at step 314.

For suspicious microcalcification detection, the ROI-level processing may include (i) applying connectivity-based region growing to the pixels of interest to form candidate microcalcification spots, (ii) clustering the candidate microcalcification spots including providing local attention to detect potentially more subtle nearby microcalcification spots (for example, using an adapted version of the local attention algorithm described in the commonly assigned U.S. Pat. No. 6,014,452, which is incorporated by reference herein), (iii) computing a plurality of features characterizing the microcalcification spots/clusters, and (iv) classifying the spots/clusters as being CAD detections, or not being CAD detections, based on those computed features. For suspicious mass detection, the ROI-level processing may include (i) grouping the pixels of interest into candidate masses, (ii) computing a plurality of features characterizing the candidate masses, and (iii) classifying the masses as being CAD detections, or not being CAD detections, based on the computed features.

Importantly, for both microcalcification and mass detection, the necessary ROI-level computer code often involves complex, time consuming, many-nested routines, and the magnitude of this computational complexity gets larger with the number of different areas of pixels of interest provided by the pixel-level analysis stage. Accordingly, it is crucial for those pixels of interest to be identified in a judicious manner at step 304.

Figure 4:
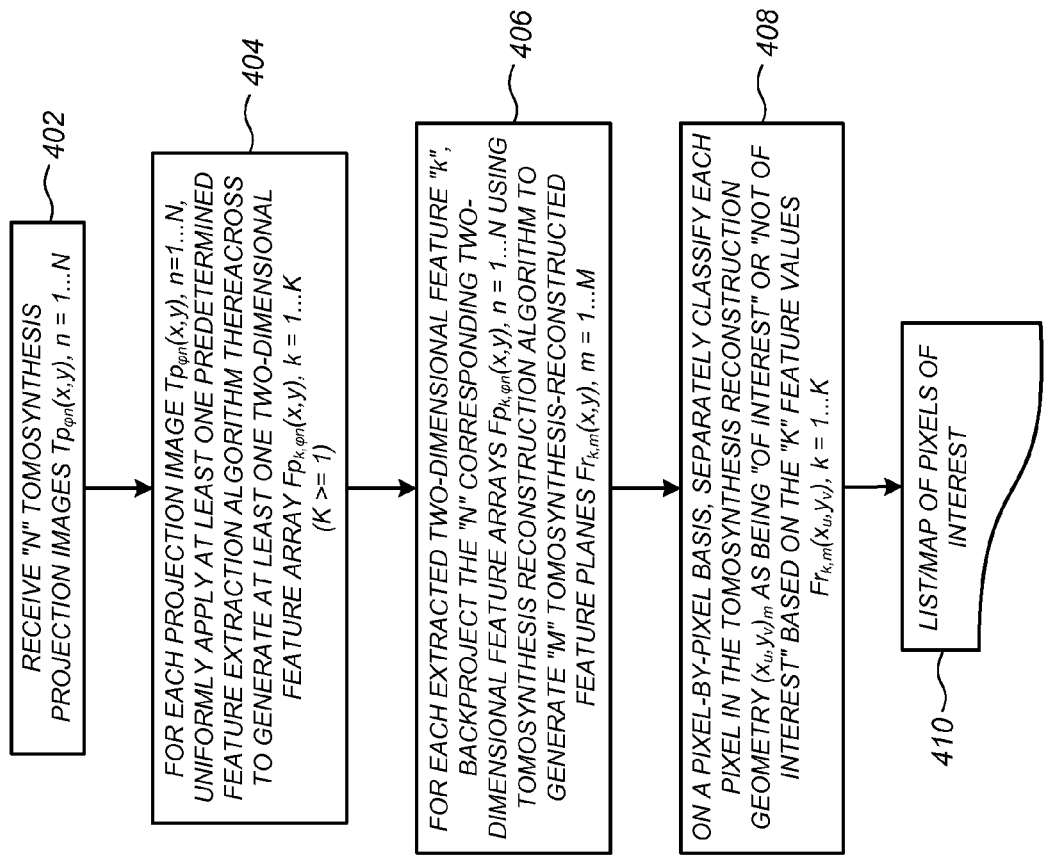
FIG. 4 illustrates pixel-level analysis steps of an x-ray tomosynthesis CAD algorithm according to a preferred embodiment.

FIG. 4 illustrates pixel-level processing in an x-ray tomosynthesis CAD algorithm according to a preferred embodiment. At step 402, the "N" tomosynthesis projection images $Tp_{\phi n}(x,y)$, n=1 . . . N, are received. At step 404, a predetermined number "K" (K≧1) of predetermined feature extraction algorithms are applied to each tomosynthesis projection image to generate, for an $n^{th}$ projection image, "K" corresponding two-dimensional feature arrays $Fp_{k,\phi n}(x,y)$, k=1 . . . K. At step 406, for each $k^{th}$ two-dimensional extracted feature, the "N" corresponding two-dimensional feature arrays $Fp_{k,\phi n}(x,y)$, n=1 . . . N, are backprojected according to a predetermined tomosynthesis reconstruction algorithm to generate a predetermined number "M" tomosynthesis-reconstructed feature arrays $Fr_{k,m}(x,y)$, m=1 . . . M. Any of a variety of known tomosynthesis reconstruction algorithms may be used without departing from the scope of the present teachings including, but not limited to, simple backprojection algorithms, filtered backprojection algorithms, cone-beam filtered backprojection algorithms, order-statistics based backprojection algorithms, and matrix inversion tomosynthesis algorithms. As described supra with respect to FIG. 2, the imaged breast volume has a three-dimensional geometry characterized by a number of levels and a number of pixels per level. Preferably, the plurality of two-dimensional tomosynthesis reconstructed feature arrays collectively occupy that three-dimensional geometry so that pixels corresponding to all clinically relevant portions of the breast volume will be considered in the determination of the initial pixels of interest.

At step 408, each pixel $(x_u, y_v)_m$ in the three-dimensional breast geometry is classified as being a pixel of interest, or not being a pixel of interest, based on the "K" feature values $Fr_{k,m}(x,y)$, k=1 . . . K at that pixel location. After all pixels in the three-dimensional breast geometry are processed, a resultant list or map of the identified pixels of interest are provided at step 410. Any of a variety of known classifier types can be used without departing from the scope of the present teachings, ranging from a simple global single-feature threshold to more complex classifier types including, but not limited to, rule-based classifiers, decision trees, artificial neural networks, and support vector machines.

FIG. 5 illustrates a method for computing a projection quantum noise compensated microcalcification feature array from a tomosynthesis projection image according to a preferred embodiment. When backprojecting such projection quantum noise compensated microcalcification feature arrays according to one or more of the preferred embodiments a particularly quantum noise-tolerant yet sensitive way of identifying pixels of interest is achieved. In the following description of FIG. 5, the projection quantum noise compensated microcalcification feature array is arbitrarily assigned a feature index k=1.

At step 502, an $n^{th}$ projection image $Tp_{\phi n}(x,y)$ is received. At step 504, the projection image $Tp_{\phi n}(x,y)$ is filtered with a microcalcification contrast-enhancing filter which can be, for example, a difference of Gaussians filter sized according to an expected range of microcalcification sizes, to generate a microcalcification contrast-enhanced array $MCEF_n(x,y)$. At step 506, the projection image $Tp_{\phi n}(x,y)$ is filtered with a smoothing filter, such as a box filter having a size greater than the expected range of microcalcification sizes, to generate a smoothed array $SF_n(x,y)$. At step 508, an $n^{th}$ lookup table $LUT_n$(pixval) is generated based on computed statistics of the arrays $MCEF_n(x,y)$ and $SF_n(x,y)$ as described further with respect to FIG. 6, infra. Finally, at step 510, an $n^{th}$ projection quantum noise compensated microcalcification feature array $Fp_{1,\phi n}(x,y)$ is computed as $MCEF_n(x,y)/LUT_n(SF_n(x,y))$, where the subscript "1" indicates the feature index k=1 representing this particular feature. The resultant "N" projection quantum noise compensated microcalcification feature arrays $Fp_{1,\phi n}(x,y)$, $n=1 \ldots N$, can then be backprojected according to step 406 of FIG. 4, supra, to generate a predetermined number "M" of tomosynthesis reconstructed quantum noise compensated microcalcification feature arrays $Fr_{1,m}(x,y)$, $m=1 \ldots M$, and a classifier (such as a global threshold) can then be applied to all pixels of all "M" levels to identify the pixels of interest in the three-dimensional breast geometry.

FIG. 6 illustrates a conceptual scatter plot corresponding to the lookup table generation method of step 508 of FIG. 5, each point in the scatter plot representing one pixel $(x_u, y_v)_n$ in the $n^{th}$ projection image and having an ordinate of $MCEF_n(x,y)$ and an abscissa of $SF_n(x,y)$. According to a preferred embodiment, for any particular pixel value present in the $SF_n(x,y)$ array, such as $pixval_1$, the lookup table $LUT_n$(pixval$_1$) is proportional to a statistical variation measure, such as standard deviation, of the values of $MCEF_n(x,y)$ for all pixels in the $n^{th}$ projection image for which $SF_n(x,y)=pixval_1$. Optionally, a curve-fitting algorithm can be applied to $LUT_n$(pixval) to correct local anomalies that may be present therein, with the fitted curve being used as the lookup table.

In an alternative preferred embodiment (not shown), the projection quantum noise compensated microcalcification feature array $Fp_{1,\phi n}(x,y)$ is computed for each $n^{th}$ projection image in a manner similar to the method of FIGS. 5-6, with the exception that the computation takes into account the joint quantum noise statistics of all N projection images put together. More particularly, instead of using a different lookup table $LUT_n(x,y)$ for each $n^{th}$ projection image, a single lookup table LUT(x,y) is generated and used for all N projection images, i.e., $Fp_{1,\phi n}(x,y)=MCEF_n(x,y)/LUT(SF_n(x,y))$. Generation of the single lookup table $LUT(SF_n(x,y))$ is similar to that shown in FIG. 6, except that the scatter plot of $MCEF_n(x,y)$ versus $SF_n(x,y)$ is generated using all pixels from all N projection images $n=1 \ldots N$ instead of just one set of pixels from one projection image.

According to another preferred embodiment relevant to suspicious mass detection, each of the "N" tomosynthesis projection images $Tp_{\phi n}(x,y)$ is processed to produce a plurality "K" of projection mass-related feature arrays $Fp_{k,\phi n}(x,y)$, $k=1 \ldots K$. Then, for each $k^{th}$ mass-related feature, the resultant "N" projection mass-related feature arrays $Fp_{k,\phi n}(x,y)$ can then be backprojected according to step 406 of FIG. 4, supra, to generate a predetermined number "M" of tomosynthesis-reconstructed mass-related feature arrays $Fr_{k,m}(x,y)$, $m=1 \ldots M$. For each pixel $(x_u, y_v)_m$ in the three-dimensional breast geometry, a classifier algorithm is then applied to the "K" feature values $Fr_{k,m}(x,y)$, $k=1 \ldots K$ to determine whether that pixel is a pixel of interest for suspicious mass detection purposes.

By way of example and not by way of limitation, the above plurality of projection mass-related feature arrays can include a projection mass density metric array $Fp_{1,\phi n}(x,y)=G1p_n(x,y)$, a projection mass isotropy metric array $Fp_{2,\phi n}(x,y)=G2p_n(x,y)$, a projection stellateness magnitude metric array $Fp_{3,\phi n}(x,y)=F1p_n(x,y)$, and a projection stellateness isotropy metric array $Fp_{4,\phi n}(x,y)=F2p_n(x,y)$, where the functions denoted G1, G2, F1, and F2 are adapted from like functions described in the commonly assigned U.S. Pat. No. 6,014,452, which is incorporated by reference herein. After backprojection, the resultant tomosynthesis-reconstructed mass-related feature planes are, respectively, a tomosynthesis reconstructed mass density metric array $Fr_{1,m}(x,y)=G1r_m(x,y)$, a tomosynthesis reconstructed mass isotropy metric array $Fr_{2,m}(x,y)=G2r_m(x,y)$, a tomosynthesis reconstructed stellateness magnitude metric array $Fr_{3,m}(x,y)=F1r_m(x,y)$, and a tomosynthesis reconstructed stellateness isotropy metric array $Fr_{4,m}(x,y)=F2r_m(x,y)$.

Advantageously, in an x-ray CAD algorithm according to one or more of the preferred embodiments, it is not required that any a priori searching or decision making take place in the three-dimensional breast to identify particular locations of interest prior to the backprojecting process. Rather, the preferred embodiments provide a forward, systematic, efficient way of determining a set of pixels of interest (and thus, conversely, to eliminate a very large set of pixels that are not of interest) for the entire three-dimensional breast geometry, to serve as the set of starting pixels for the complex and time-consuming ROI-level downstream processes in the CAD algorithm. Moreover, in determining an initial of pixels of interest for microcalcification detection based on backprojection of quantum noise-compensated microcalcification feature arrays according to one or more of the preferred embodiments, an advantageous combination of efficiency and noise tolerance is provided. For one preferred embodiment, the spatial extent of the three-dimensional breast geometry can simply correspond to the entire space between the x-ray tomosynthesis compression paddles. For another preferred embodiment, an initial three-dimensional outline of the breast volume can be estimated based on a the two-dimensional extent of the breast tissue in one or more of the projection images, with the three-dimensional outline serving as the basis for the three-dimensional breast geometry.

Whereas many alterations and modifications of the preferred embodiments will no doubt become apparent to a person of ordinary skill in the art after having read the foregoing description, it is to be understood that the particular embodiments shown and described by way of illustration are in no way intended to be considered limiting. By way of example, although particularly advantageous in the context of breast x-ray tomosynthesis, one or more of the above-described preferred embodiments is readily applicable to other tomographic medical imaging modalities for the breast or other body parts that are based on the acquisition of projection images followed by filtered backprojection, iterative reconstruction, or other tomographic reconstruction algorithm to produce one or more tomography images representative of cross-sections of that body part including, such modalities including, but not limited to, x-ray CT tomography, single photon emission computed tomography (SPECT), positron emission tomography (PET), and transmission electron tomography (TEM), and such applications are within the scope of the present teachings. In such applications, for each of a plurality of projection images corresponding to that modality, the projection image is processed according to at least one predetermined feature extraction algorithm to generate at least one projection feature array corresponding thereto, and then for each of the at least one predetermined features extracted, the plurality of corresponding projection feature arrays are backprojected according to a predetermined tomographic reconstruction algorithm to form a plurality of two-dimensional tomographic feature arrays.

By way of further example, although the at least one tomosynthesis reconstructed feature array according to one or more of the preferred embodiments is of particular advantageous application in the processing thereof to individually classify each pixel in the three-dimensional geometry as being either a pixel of interest or not a pixel of interest for subsequent application to downstream ROI-level processing algorithms, in other preferred embodiments the at least one tomosynthesis reconstructed feature array can, alternatively or in conjunction therewith, serve as a basis for any of a variety of other local or regional classification processes. Thus, reference to the details of the described embodiments are not intended to limit their scope, which is limited only by the scope of the claims set forth below.

What is claimed is:

1. A method for computer-aided detection (CAD) of anatomical abnormalities in a breast volume based on a plurality of two-dimensional x-ray tomosynthesis projection images thereof acquired at a respective plurality of x-ray tomosynthesis projection angles, comprising:
    for each of the plurality of projection images, processing that projection image separately from the other projection images according to at least one predetermined feature extraction algorithm to generate at least one projection feature array corresponding thereto;
    for each of the at least one predetermined features extracted, backprojecting the plurality of corresponding projection feature arrays according to a predetermined tomosynthesis reconstruction algorithm to form a plurality of two-dimensional tomosynthesis reconstructed feature arrays, the imaged breast volume having a three-dimensional geometry characterized by a number of levels and a number of pixels per level, wherein said plurality of two-dimensional tomosynthesis reconstructed feature arrays collectively occupy said three-dimensional geometry;
    individually classifying each pixel in each level of said three-dimensional geometry as being one of (i) a pixel of interest and (ii) not a pixel of interest based upon the at least one tomosynthesis reconstructed feature array value corresponding to that pixel location; and
    generating CAD detections for the breast volume based on the identified pixels of interest.

2. The method of claim 1, wherein said at least one predetermined feature extraction algorithm performed on each said projection image comprises a quantum noise-compensating microcalcification enhancement algorithm designed to generate a projection quantum noise-compensated microcalcification feature array.

3. The method of claim 2 wherein said quantum noise-compensating microcalcification enhancement algorithm comprises, for an $n^{th}$ of said projection images, the steps of:
    generating a microcalcification contrast-enhanced version $MCEF_n(x,y)$ of the $n^{th}$ projection image using a high-pass convolution kernel sized according to an expected microcalcification size range;
    generating a smoothed version $SF_n(x,y)$ of the $n^{th}$ projection image using a smoothing filter that is relatively large compared to the expected microcalcification size range;
    generating a lookup table $LUT_n(pixval)$ that, for an argument value pixval, corresponds to a statistical variation measure of $MCEF_n(x,y)$ for those pixels in the $n^{th}$ projection image for which $SF_n(x,y)$ is equal to the pixval; and
    setting said projection quantum noise-compensated microcalcification feature array equal to $MCEF_n(x,y)/SF_n(x,y)$ for each pixel $(x,y)_n$ in the $n^{th}$ projection image.

4. The method of claim 3, said backprojection forming a plurality of tomosynthesis reconstructed quantum noise-compensated microcalcification feature arrays, wherein said individually classifying each pixel in each level of said three-dimensional geometry comprises applying a global threshold value to each pixel in said plurality of tomosynthesis reconstructed quantum noise-compensated microcalcification feature arrays.

5. The method of claim 3, wherein said generating CAD detections for the breast volume based on the identified pixels of interest comprises grouping adjacent ones of said pixels of interest into candidate microcalcification spots, clustering said candidate microcalcification spots, computing a plurality of features characterizing said microcalcification spots/clusters, and classifying said spots/clusters as being CAD detections, or not being CAD detections, based on said computed features.

6. The method of claim 1, wherein said individually classifying each pixel as being one of (i) a pixel of interest and (ii) not a pixel of interest consists of a non-neighborhood process based solely on the least one tomosynthesis reconstructed feature array value at that pixel location.

7. The method of claim 6, wherein said three-dimensional geometry occupied by said plurality of two-dimensional tomosynthesis reconstructed feature arrays spans substantially an entirety of the imaged breast volume at a diagnostically sufficient resolution for suspicious abnormality detection, whereby said pixels of interest are identified without requiring either of (a) prior reconstruction of a tomosynthesis reconstructed image volume from said plurality of projection images, or (b) neighborhood-based processing of the two-dimensional tomosynthesis reconstructed feature arrays.

8. The method of claim 1, wherein said generating CAD detections for the breast volume based on the identified pixels of interest comprises discarding from consideration all pixels classified as not being of interest.

9. The method of claim 1, further comprising determining an outline of the breast volume based on a two-dimensional extent of breast tissue appearing in one or more of said projection images, wherein said three-dimensional breast geometry is based on said determined outline.

10. The method of claim 1, further comprising backprojecting the plurality of projection image arrays according to said predetermined tomosynthesis reconstruction algorithm to form a plurality of two-dimensional tomosynthesis reconstructed images, wherein said individually classifying each pixel in each level of said three-dimensional geometry is further based upon a pixel value of the tomosynthesis reconstructed image at that pixel location and level.

11. The method of claim 1, wherein said at least one predetermined feature extraction algorithm is configured to generate, for an $n^{th}$ of said projection images, each of a projection mass density metric array $G1p_n(x,y)$, a projection mass isotropy metric array $G2p_n(x,y)$, a projection stellateness magnitude metric array $F1p_n(x,y)$, and a projection stellateness isotropy metric array $F2p_n(x,y)$.

12. The method of claim 11, said backprojection forming, for an $m^{th}$ level of said tomosynthesis reconstruction geometry, a tomosynthesis reconstructed mass density metric array $G1r_m(x,y)$, a tomosynthesis reconstructed mass isotropy metric array $G2r_m(x,y)$, a tomosynthesis reconstructed stellateness magnitude metric array $F1r_m(x,y)$, and a tomosynthesis reconstructed stellateness isotropy metric array $F2r_m(x,y)$, wherein said individually classifying each pixel for said $m^{th}$ level in said three-dimensional geometry comprises applying said $G1r_m(x,y)$, $G2r_m(x,y)$, $F1r_m(x,y)$, and $F2r_m(x,y)$ features to a predetermined classifier algorithm.

13. The method of claim 12, wherein said predetermined classifier algorithm is selected from the group consisting of: artificial neural networks, rule-based classifiers, decision trees, and support vector machines.

14. The method of claim 12, wherein said generating CAD detections for the breast volume based on the identified pixels of interest comprises grouping said pixels of interest into candidate masses, computing a plurality of features characterizing said candidate masses, and classifying said masses as being CAD detections, or not being CAD detections, based on said computed features.

15. A system for detecting suspicious microcalcifications in a breast volume based on a plurality of two-dimensional x-ray tomosynthesis projection images thereof acquired at a respective plurality of x-ray tomosynthesis projection angles, the system comprising a processor programmed to perform the steps of:
 jointly processing the plurality of projection images to generate a noise compensation function based on joint noise statistics in the plurality of projection images;
 processing each of said plurality of projection images using a microcalcification-enhancing filter, a spatial smoothing filter, and said noise compensation function to generate a respective plurality of projection noise-compensated microcalcification feature arrays;
 backprojecting said plurality of projection noise-compensated microcalcification feature arrays according to a predetermined tomosynthesis reconstruction algorithm to form a plurality of two-dimensional tomosynthesis reconstructed feature arrays, the imaged breast volume having a three-dimensional geometry characterized by a number of levels and a number of pixels per level, wherein said plurality of two-dimensional tomosynthesis reconstructed feature arrays collectively occupy said three-dimensional geometry;
 individually classifying each pixel in each level of said three-dimensional geometry as being one of (i) a pixel of interest and (ii) not a pixel of interest based upon the at least one tomosynthesis reconstructed feature array value corresponding to that pixel location; and
 processing the identified pixels of interest to detect suspicious microcalcifications in the breast volume.

16. The system of claim 15, said plurality of projection images having "N" members, wherein said jointly processing said N projection images to generate said noise compensation function comprises:
 for each $n^{th}$ projection image, n=1 . . . N, generating a microcalcification contrast-enhanced version $MCEF_n(x,y)$ thereof using a high-pass convolution kernel sized according to an expected microcalcification size range;
 for each $n^{th}$ projection image, n=1 . . . N, generating a smoothed version $SF_n(x,y)$ thereof using a smoothing filter that is relatively large compared to the expected microcalcification size range; and
 generating said noise compensation function as a lookup table LUT(pixval) that, for each argument value pixval, corresponds to a statistical variation in the values of $MCEF_n(x,y)$ for all pixels in the N projection images having corresponding values of $SF_n(x,y)$ that are equal to pixval.

17. The system of claim 16, wherein for each pixel $(x,y)_n$ in each $n^{th}$ projection image, said noise-compensated microcalcification feature arrays is assigned the value of $MCEF_n(x,y)/LUT(SF_n(x,y))$.

18. The system of claim 17, wherein said individually classifying each pixel as being one of (i) a pixel of interest and (ii) not a pixel of interest consists of a non-neighborhood process based solely on the tomosynthesis reconstructed feature array value at that pixel location, and wherein said three-dimensional geometry occupied by said plurality of two-dimensional tomosynthesis reconstructed feature arrays spans substantially an entirety of the imaged breast volume at a diagnostically sufficient resolution for microcalcification detection, whereby said pixels of interest are identified without requiring either of (a) prior reconstruction of a tomosynthesis reconstructed image volume from said plurality of projection images, or (b) neighborhood-based processing of the two-dimensional tomosynthesis reconstructed feature arrays.

19. A computer readable medium embodying a computer program product for performing computer-aided detection (CAD) of anatomical abnormalities in a breast volume based on a plurality of two-dimensional x-ray tomosynthesis projection images thereof acquired at a respective plurality of x-ray tomosynthesis projection angles, comprising:
 computer code for programming a tomosynthesis processor to process each of the plurality of projection images according to at least one predetermined feature extraction algorithm to generate at least one projection feature array corresponding thereto;
 computer code for programming a tomosynthesis processor to back project, for each of the at least one predetermined features extracted, the plurality of corresponding projection feature arrays according to a predetermined tomosynthesis reconstruction algorithm to form a plurality of two-dimensional tomosynthesis reconstructed feature arrays, the imaged breast volume having a three-dimensional geometry characterized by a number of levels and a number of pixels per level, wherein said plurality of two-dimensional tomosynthesis reconstructed feature arrays collectively occupy said three-dimensional geometry;
 computer code for programming a tomosynthesis CAD processor to individually classify each pixel in each level of said three-dimensional geometry as being one of (i) a pixel of interest and (ii) not a pixel of interest based upon the at least one tomosynthesis reconstructed feature array value corresponding to that pixel location; and
 computer code for programming a tomosynthesis CAD processor to generate CAD detections for the breast volume based on the identified pixels of interest.

20. A computer readable medium of claim 19, wherein said predetermined tomosynthesis reconstruction algorithm used in said computer code for backprojecting is selected from the group consisting of: simple backprojection, filtered backprojection, cone-beam filtered backprojection, order-statistics based backprojection, and matrix inversion tomosynthesis.

* * * * *